US008909338B2

(12) United States Patent
Thakur et al.

(10) Patent No.: US 8,909,338 B2
(45) Date of Patent: Dec. 9, 2014

(54) ELECTRODE DISPLACEMENT DETECTION

(71) Applicant: Cardiac Pacemakers, Inc., St. Paul, MN (US)

(72) Inventors: Pramodsingh Hirasingh Thakur, Woodbury, MN (US); Viktoria A. Averina, Roseville, MN (US); Qi An, Blaine, MN (US); John D. Hatlestad, Maplewood, MN (US); Lili Liu, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/949,334

(22) Filed: Jul. 24, 2013

(65) Prior Publication Data

US 2014/0031888 A1    Jan. 30, 2014

Related U.S. Application Data

(60) Provisional application No. 61/675,409, filed on Jul. 25, 2012.

(51) Int. Cl.
*A61N 1/00*    (2006.01)
*A61N 1/37*    (2006.01)
*A61N 1/08*    (2006.01)

(52) U.S. Cl.
CPC .............. *A61N 1/37* (2013.01); *A61N 2001/083* (2013.01)
USPC ........................................................ 607/28

(58) Field of Classification Search
CPC . A61N 1/37; A61N 2001/083; A61N 1/3712; A61N 1/371; A61N 1/3714; A61N 1/372
USPC ........................................................ 607/28
See application file for complete search history.

(56) References Cited

U.S. PATENT DOCUMENTS

| 5,284,136 | A | 2/1994 | Hauck et al. |
| 6,076,015 | A | 6/2000 | Hartley et al. |
| 6,490,486 | B1 | 12/2002 | Bradley |
| 6,937,901 | B2 | 8/2005 | Zhu et al. |
| 7,387,610 | B2 | 6/2008 | Stahmann et al. |
| 7,559,901 | B2 | 7/2009 | Maile et al. |

(Continued)

FOREIGN PATENT DOCUMENTS

| WO | WO-9842406 A1 | 10/1998 |
| WO | WO-2006060426 A2 | 6/2006 |
| WO | WO-2014018592 A1 | 1/2014 |

OTHER PUBLICATIONS

"International Application Serial No. PCT/US2013/051772, International Search Repot mailed Oct. 17, 2013", 4 pgs.

(Continued)

*Primary Examiner* — George Manuel
(74) *Attorney, Agent, or Firm* — Schwegman Lundberg & Woessner, P.A.

(57) ABSTRACT

Electrode displacement can be detected using a thoracic impedance or conductivity signal. The thoracic impedance or conductivity signal can be filtered to attenuate cardiac contraction (stroke) and respiration components. A fluid status component of the thoracic impedance or conductivity signal can be used to detect a posture-shift related electrode displacement, such as can result from left ventricular/coronary sinus (LV/CS) lead pullback upon a recumbent to upright posture shift.

20 Claims, 6 Drawing Sheets

(56) References Cited

U.S. PATENT DOCUMENTS

| | | |
|---|---|---|
| 7,640,056 B2 | 12/2009 | Belalcazar |
| 7,662,104 B2 | 2/2010 | Siejko et al. |
| 7,848,811 B2 | 12/2010 | Moon et al. |
| 7,873,410 B2 | 1/2011 | Cho et al. |
| 7,991,484 B1 | 8/2011 | Sengupta et al. |
| 8,165,840 B2 | 4/2012 | Hatlestad et al. |
| 2005/0004611 A1 | 1/2005 | Edwards et al. |
| 2006/0106445 A1 | 5/2006 | Woollett |
| 2006/0224222 A1 | 10/2006 | Bradley |
| 2008/0188909 A1 | 8/2008 | Bradley |
| 2010/0087891 A1 | 4/2010 | Levine et al. |
| 2010/0114204 A1* | 5/2010 | Burnes et al. ............... 607/4 |
| 2010/0152801 A1 | 6/2010 | Koh et al. |
| 2011/0066203 A1 | 3/2011 | Rosenberg et al. |
| 2011/0118803 A1 | 5/2011 | Hou et al. |
| 2011/0125207 A1 | 5/2011 | Nabutovsky et al. |
| 2011/0213260 A1 | 9/2011 | Keel et al. |

OTHER PUBLICATIONS

"International Application Serial No. PCT/US2013/051772, Written Opinion mailed Oct. 17, 2013", 5 pgs.

* cited by examiner

| Loose Lead | Lead Number | Pair Wise Correlation |
|---|---|---|
| RV Lead | 138A | Corr (LVz, RVz) < 0 & <br> Corr (RVz, RAz) < 0 & <br> Corr (RAz, LVz) > 0 |
| LV Lead | 138B | Corr (LVz, RVz) < 0 & <br> Corr (LVz, RAz) < 0 & <br> Corr (RAz, RVz) > 0 |
| RA Lead | 138C | Corr (RAz, RVz) < 0 & <br> Corr (LVz, RAz) < 0 & <br> Corr (LVz, RVz) > 0 |

| Loose Lead | Lead Number | Pair Wise Correlation |
|---|---|---|
| RV | 138A | Corr (RVz, P(R)) < 0 |
| LV | 138B | Corr (LVz, P(R)) < 0 |
| RA | 138C | Corr (RAz, P(R)) < 0 |

ELECTRODE DISPLACEMENT DETECTION

CLAIM OF PRIORITY

This application claims the benefit of priority under 35 U.S.C. §119(e) of U.S. Provisional Patent Application Ser. No. 61/675,409, entitled "ELECTRODE DISPLACEMENT DETECTION", filed on Jul. 25, 2012, which is herein incorporated by reference in its entirety.

BACKGROUND

A cardiac rhythm management (CRM) system can include an intravascularly delivered coronary sinus (CS) left ventricular (LV) lead connected to a pectorally or abdominally subcutaneously implanted electronics unit. The CS/LV lead can be introduced into the CS vessel via the right atrium (RA). The CS/LV lead can be positioned such that electrodes at or near the distal end of the CS lead can be located in the CS tributary great cardiac vein (GCV) in association with the LV myocardium. Electrostimulations delivered from such CS/LV electrodes can be used to capture the LV myocardium. Such electrostimulations can be used to provide cardiac resynchronization therapy (CRT) to adjust the LV contraction rate, to spatially coordinate the LV contraction (such as within the LV or with a desired synchronization with a right ventricular (RV) contraction), or both.

A lead can be held in place screwing in a tine into the heart wall to secure the lead at a desired location. Screwing in a tine is less easy to do within vasculature, such as the CS vessel, than within an atrial or ventricular heart chamber. A more convenient approach can be to provide a shape-memory characteristic to the lead body. For example, a CS/LV lead can be configured with a shape memory characteristic such that, after insertion, the CS/LV lead can relax to assume a gradual spiral. The gradual spiral shape memory characteristic can help mechanically bias the lead against the inner wall of the CS to help secure the lead at a desired location.

Movement or dislodgement of a CS/LV lead can cause unwanted electrostimulation of the phrenic nerve, rather than the desired electrostimulation of myocardial tissue to elicit a heart contraction. Phrenic nerve stimulation can cause a hiccup-like contraction of the patient's diaphragm, which can be annoying or discomforting. Moreover, if the desired myocardial electrostimulation becomes suboptimal or ineffective, the beneficial effects of CRT can similarly become suboptimal or ineffective.

Edwards et al. U.S. Patent Pub. No. 2005/0004611 is directed toward a system and method for detecting dislodgement of an implantable medical device, including generating a current signal within the body and measuring certain response voltages.

Bradley U.S. Pat. No. 6,490,486 is directed toward an implantable cardiac stimulation device and method that monitors displacement of an implanted lead, including using an impedance measurement measured using the lead over a cardiac cycle of the patient's heart.

Rosenberg et al. U.S. Patent Pub. No. 2011/0066203 is directed toward an electrode and lead stability indexes and stability maps based on localization system data, including measuring electrical potentials to determine acute and chronic stability of an electrode.

Levine et al. U.S. Patent Pub. No. 2010/0087891 is directed toward systems and method for diagnosing an implantable medical device, including detecting lead dislodgement based upon measured parameters.

Cho et al. U.S. Pat. No. 7,873,410 is directed toward an implantable medical device with electromechanical delay measurement for lead position or dislodgement and ventricular dyssynchrony detection.

OVERVIEW

An intrathoracic impedance or conductivity signal can include variations that can provide information about heart contractions (with frequency content at the subject's heart contraction frequency). The intrathoracic impedance or conductivity signal can also include variations that can provide information about breathing (with frequency content at the subject's respiration frequency, which is generally lower than the subject's heart contraction frequency). At still lower frequencies than the heart contraction or respiration variations (e.g., at lower DC or near-DC frequencies), the intrathoracic impedance or conductivity signal can include variations that can provide information about the subject's thoracic fluid status. A wet lung is more conductive than a dry lung. Therefore, a wet lung should exhibit a relatively lower DC or near-DC intrathoracic impedance (or higher intrathoracic conductivity) than a dry lung.

The DC or near-DC intrathoracic impedance information representative of a subject's thoracic fluid status can be affected by the subject's posture. When a subject is in an upright posture, fluid drains away from the thorax, such as toward the lower extremities. This should result in a dryer thorax, and a higher DC or near-DC value of intrathoracic impedance. When a subject is in a recumbent posture, fluid drains into the thorax, such as from the lower extremities. This should result in a wetter thorax, and a lower DC or near-DC value of intrathoracic impedance. A change in the subject's posture can also be accompanied by a compensatory change in the subject's vascular tone (e.g., vasodilation or vasoconstriction). However, such a responsive change in the subject's vascular tone is generally not abrupt, but instead is a more gradual response, which exhibits a corresponding gradual change in impedance.

However, in observing experimentally-collected intrathoracic impedance data, the present inventors have recognized the presence of an unexpected, unusual intrathoracic impedance variation in posture in at least one subject: a substantially instantaneous significant (e.g., about a 50% change) decrease in DC or near-DC intrathoracic impedance in response to the subject changing from a recumbent posture to an upright posture, instead of the expected increase from fluid draining away from the thorax to the lower extremities. In the at least one subject in which this unusual effect was observed, the DC or near-DC intrathoracic impedance measurements determined using LV/CS electrodes were affected in this unusual manner, but the DC or near-DC intrathoracic impedance measurements determined using RV electrodes were not affected in this unusual manner.

Without being bound by theory, the present inventors have recognized that the above unusual effect of posture on LV/CS DC or near-DC intrathoracic impedance or conductivity measurements likely arise from the LV/CS lead moving within the CS or its GCV tributary. When the subject transitions from a recumbent posture to an upright posture, it is believed that the heart can move slightly downward, due to gravity. The LV/CS lead, which is being held in place by mechanical biasing against the vessel wall by the gradual spiral shape memory lead characteristic, can be abruptly pulled back proximally into a broader section of the CS or GCV vessel when the patient transitions from a recumbent posture into an upright posture. It is believed that when the electrodes on the LV/CS lead are located in the broader portion of the vessel, they will be surrounded by more blood and less vessel wall. Because blood is more conductive than vessel wall tissue, such pulling back of the LS/CS lead electrodes into a broader segment of the vessel can result in an abrupt decrease in DC or near-DC intrathoracic impedance upon the subject's transition from a recumbent posture to an upright posture, which may be more noticeable than the somewhat more gradual increase in the DC or near-DC intrathoracic impedance that would be expected from thoracic fluid draining away from the subject's thorax into the subject's lower extremities upon such shift from a recumbent posture to an upright posture.

The present inventors have recognized, among other things, that this unusual effect can be used to detect electrode movement or dislodgement, such as of a LV/CS lead. This information can also be used to compensate or adjust intrathoracic impedance measurement information, or to adjust a therapy response or other function of a CRM device making use of intrathoracic impedance measurement information.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
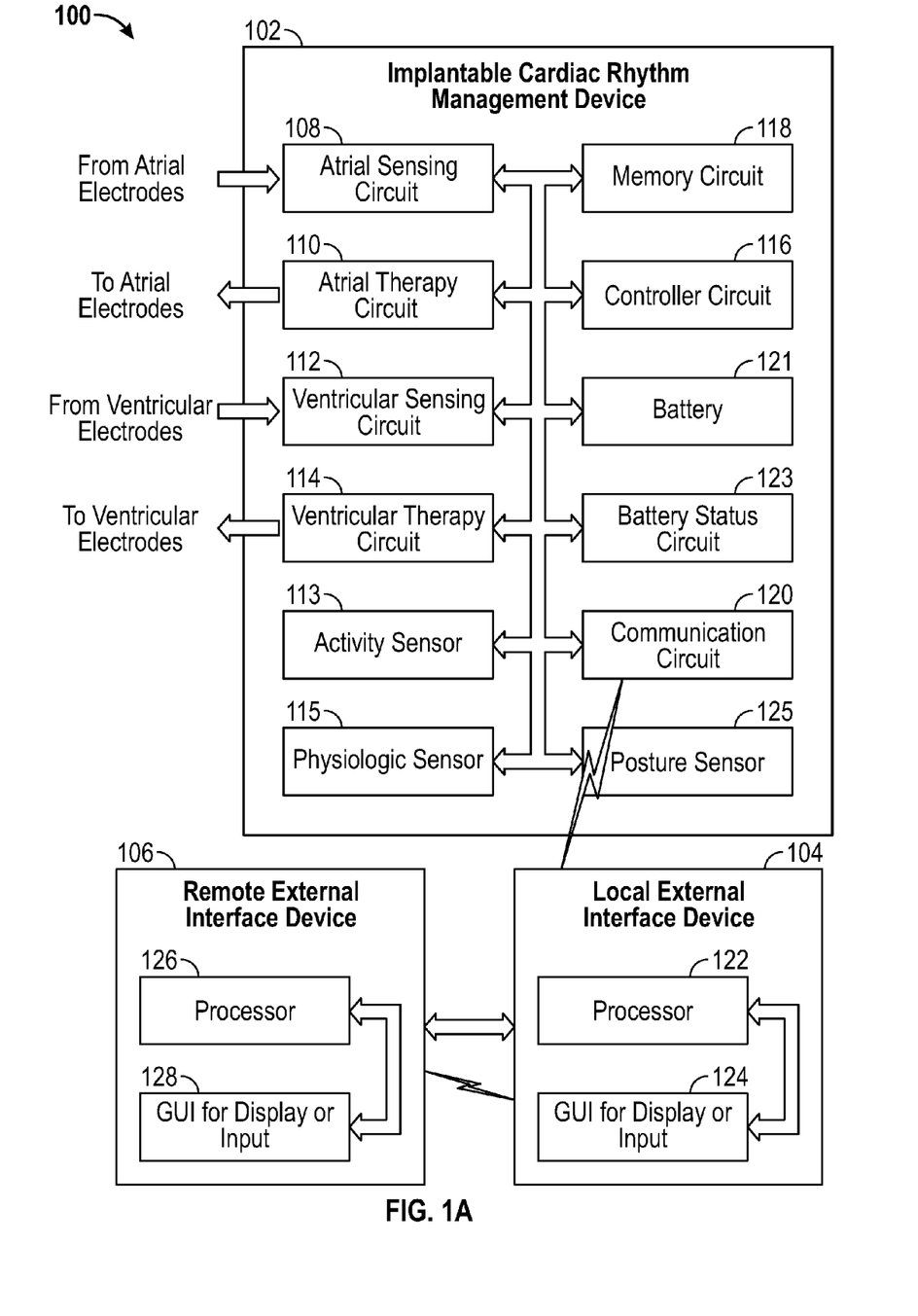
FIGS. 1A-1B shows an example of portions of a cardiac function management system and an environment in which it is used.
Figure 1B:
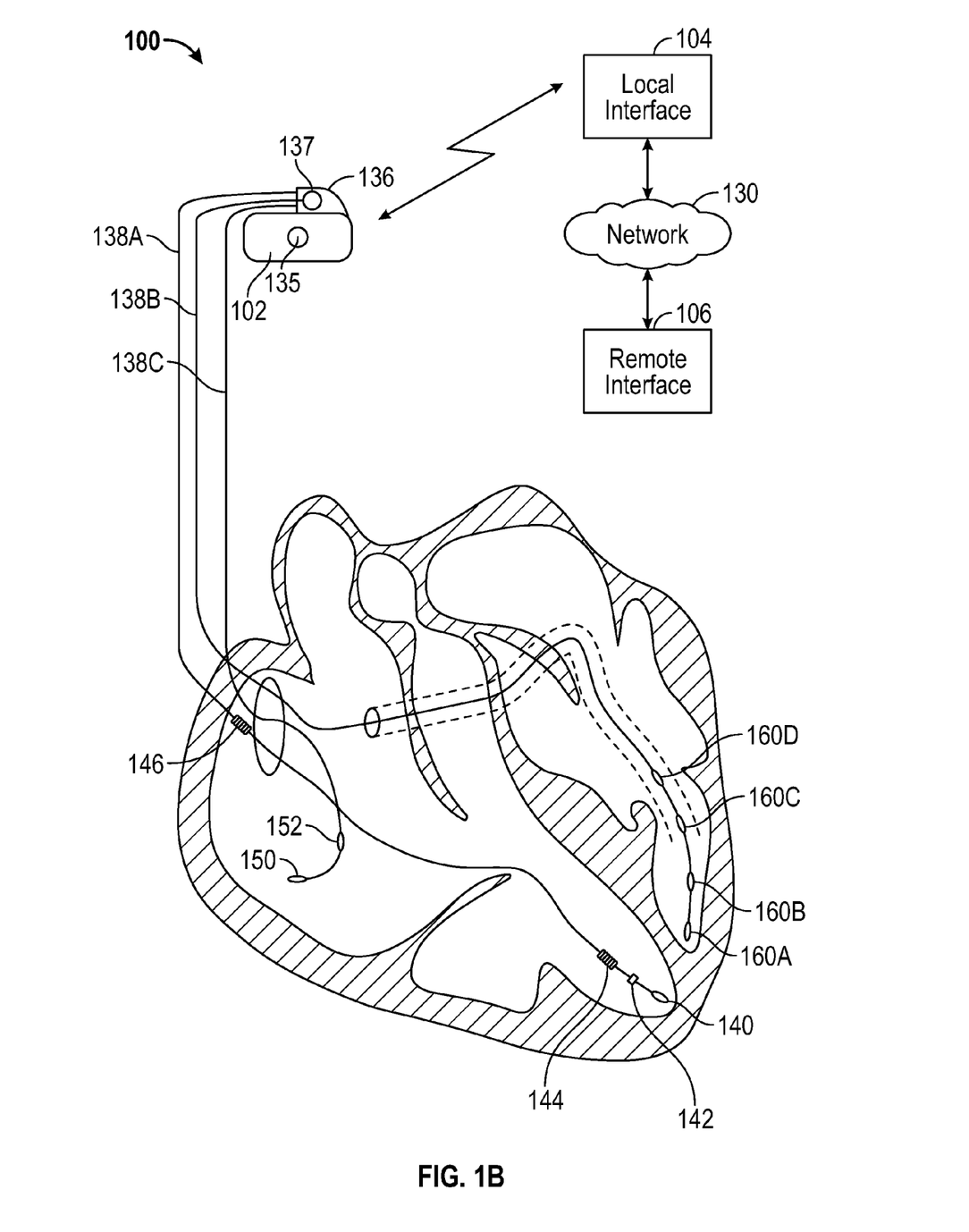

FIGS. 1A-1B show an example of portions of a cardiac function management system 100 and an environment in which it is used. The system 100 can include an ambulatory medical device, such as an external (e.g., wearable) medical device or an implantable medical device (IMD) such as an implantable cardiac rhythm or function management device 102, a local external interface device 104, and a remote external interface device 106.

The implantable device 102 can optionally include one or more of an atrial sensing circuit 108, an atrial therapy circuit 110, a ventricular sensing circuit 112, a ventricular therapy circuit 114, a controller circuit 116, a memory circuit 118, a communication circuit 120, a power source such as a battery 121, a battery status circuit 123, an activity sensor 113 configured to sense a physical activity signal of a patient or other subject, a physiologic sensor 115 configured to sense a physiologic signal (e.g., different from the physical activity signal of the subject), and a posture sensor 125.

The atrial sensing circuit 108 can include one or more channels and can be coupled to electrodes, such as an intra-atrial electrode or any other electrode that permits sensing of an intrinsic atrial cardiac signal including atrial depolarization information. The atrial therapy circuit 110 can include one or more channels and can similarly be coupled to these or other electrodes, such as for delivering pacing, cardiac resynchronization therapy (CRT), cardiac contractility modulation (CCM) therapy, defibrillation/cardioversion shocks, or other energy pulses to one or both atria.

The ventricular sensing circuit 112 can include one or more channels and can be coupled to electrodes, such as an intra-ventricular electrode, an LV/CS electrode, or any other electrode that permits sensing of an intrinsic ventricular cardiac signal including ventricular depolarization information. The ventricular therapy circuit 114 can include one or more channels and can similarly be coupled to these or other electrodes, such as for delivering pacing, cardiac resynchronization therapy (CRT), cardiac contractility modulation (CCM) therapy, defibrillation/cardioversion shocks, or other energy pulses to one or both ventricles.

The activity sensor 113 can include a single or multiple axis accelerometer, such as to sense an acceleration of the subject that is indicative of physical activity of the subject. The activity sensor 113 can also include a sensor interface circuit, configured to process the acceleration signal and provide a resulting physical activity signal. The physical activity signal can be indicative of a physical exertion of the subject. The activity sensor 113 can also be used for other purposes, such as to sense the subject's posture, heart sounds, or other information available from an acceleration signal. A separate posture sensor 125 can optionally be provided, such as a tilt-switch, a separate single or multiple axis accelerometer, or other sensor capable of providing a posture-indicative signal, either directly or extracted from other physiologic information, which can be sensed by the posture sensor 125 or obtained from the physiologic sensor 115. Some examples of posture sensor devices and methods are described in Maile et al. U.S. Pat. No. 7,559,901, Siejko et al. U.S. Pat. No. 7,662,104, Moon et al. U.S. Pat. No. 7,848,811, and Hatlestad et al. U.S. Pat. No. 8,165,840, each of which is incorporated herein by reference, including their description of posture sensing devices and methods.

The physiologic sensor 115 can include an impedance (or other physiological conductivity characteristic) sensor, a respiration sensor, or another sensor. In an example, the physiologic sensor 115 can include a respiration sensor that can sense respiration via a physiologic impedance (or other physiological conductivity characteristic) signal that can be provided by an impedance or other sensor. The impedance or other physiological conductivity sensor can include or be coupled to electrodes configured to deliver a test energy, such as a subcapture test energy delivered to the subject's thorax, and to sense a responsive voltage signal, such as indicative of the thoracic impedance or thoracic conductivity. The resulting thoracic impedance or conductivity signal can be filtered to provide information about respiration, heart contraction, or thoracic fluid accumulation. The electrodes used for impedance monitoring can include one or any combination of one or more right atrial (RA) electrodes, one or more right ventricular (RV) electrodes, one or more LV/CS electrodes such as can be located on a bipolar or quadripolar LV/CS lead, one or more wired or wireless epicardial electrodes, IMD electronics unit housing or header electrodes, or one or more other implantable or wearable electrodes. The impedance monitoring is merely an example of monitoring a physiological conductivity characteristic, other examples of which can include voltage monitoring, transimpedance monitoring, transconductance monitoring, etc. Examples of impedance monitoring devices and methods are provided in: Hauck et al. U.S. Pat. No. 5,284,136; Hartley et al. U.S. Pat. No. 6,076,015; Stahmann et al. U.S. Pat. No. 7,387,610; the disclosures of each of which are incorporated herein by reference, including their description of impedance monitoring techniques. An example of another type of physiological conductivity characteristic monitoring is provided in Belalcazar U.S. Pat. No. 7,640,056, the disclosure of which is incorporated herein by reference, including its description of fluid monitoring using another type of physiological conductivity characteristic.

In various examples, the physiologic sensor 115 can be configured to provide information about heart rate, heart rate variability, autonomic balance, heart vibrations, intracardiac pressure, thoracic fluid status, respiration, patient activity level, temperature, pH, potassium levels, oxygenation, cardiac volumes, blood pressure, or ejection fraction.

A processor or controller circuit 116 can be coupled to the atrial sensing circuit 108 and the ventricular sensing circuit 112, such as to receive information from the sensed cardiac signals. The controller circuit 116 can also be coupled to the activity sensor 113 to receive information about the subject's physical activity or exertion level. The controller circuit 116 can also be coupled to the physiologic sensor 115, such as to receive other physiologic information. Such other physiologic information can include cardiac contraction signal, such as to provide information about the subject's heart rate or interval, stroke volume, or other information available from the cardiac contraction signal. In an example, the other physiologic information can include a respiration signal, such as to provide information about the subject's breathing rate or interval, tidal volume, or other information available from the respiration signal.

The controller circuit 116 can include a signal processor circuit, such as a digital signal processor (DSP) circuit, such as for extracting a parameter from which a diagnostic indicator can be generated, such as described below. The signal processor circuit can include dedicated circuitry for performing one or more signal processing functions. The controller circuit 116 can be coupled to the atrial therapy circuit 110 and the ventricular therapy circuit 114 to provide control or triggering signals, such as to trigger timed delivery of the therapy pulses. The controller circuit 116 can be configured to provide control to help permit therapy to be effectively delivered, such as in combination with one or more other therapies (e.g., bradycardia pacing, antitachyarrhythmia pacing (ATP), cardiac resynchronization therapy (CRT), atrial or ventricular defibrillation shock therapy) or functionalities (e.g., autothreshold functionality for automatically determining pacing threshold energy, autocapture functionality for automatically adjusting pacing energy to capture the heart, etc.). In an example, this can include providing dedicated modules within the controller circuit 116, or providing executable, interpretable, or otherwise performable code to configure the controller circuit 116.

A memory circuit 118 can be included in or coupled to the controller circuit 116, such as to store control parameter values, physiological data, or other information. A communication circuit 120 can be coupled to the controller circuit 116, such as to permit radiofrequency (RF) or other wireless communication with an external device, such as the local external interface device 104 or the remote external interface device 106.

The battery 121 can include one or more batteries to provide power for the implantable device 102. In an example, the battery 121 can be rechargeable, such as by wireless transcutaneous power transmission from an external device to the implantable device 102. The battery status circuit 123 can be communicatively coupled to each of the battery 121 and the controller circuit 116, such as to determine battery status information, for example, indicative of how much energy remains stored in the battery 121. The controller circuit 116 can be configured to alter operation of the implantable device 102, such as based at least in part on the battery status information.

The local external interface device 104 can include a processor circuit 122 and a graphic user interface (GUI) 124 or like device for displaying information or receiving user input as well as a communication circuit, such as to permit wired or wireless communication with the remote external interface device 106 over a communications or computer network. Similarly, the remote external interface device 106 can include a processor circuit 126 and a graphic user interface (GUI) 128 or like device for displaying information or receiving user input as well as a communication circuit, such as to permit wired or wireless communication with the local external interface device 104 over the communications or computer network.

Because the system 100 includes processing capability in the ambulatory or implantable device 102 (e.g., provided by the controller circuit 116), the local external interface device 104 (e.g., provided by the processor 122), and the remote external interface device 106 (e.g., provided by the processor 126), various methods discussed in this document can be implemented at any of such locations, or tasks can be distributed between two or more of such locations.

FIG. 1B shows an example of an implantable device 102, which can be coupled to one or more intravascular leads, such as an RV lead 138A, a CS/LV lead 138B, or a right atrial (RA) lead 138C. The implantable device 102 can include a housing electrode 135 that can be located on an external surface of a housing carrying the electronics of the implantable device 102. A header electrode 137 can be located on a header 136 of the implantable device 102. The header 136 can extend outward from the housing. The RV lead 138A can include one or more electrodes, such as a RV tip electrode 140, a slightly more proximal RV ring electrode 142, a slightly more proximal RV first coil electrode 144, and a more proximal supraventricular second coil electrode 146. The CS/LV lead 138B can include one or more electrodes, such as electrodes 160A, 160B, 160C, and 160D (arranged distally to proximally), in a quadripolar example. Bipolar or unipolar electrode configurations are also possible. The RA lead 138C can include one or more electrodes, such as RA electrodes 150 and 152.

Figure 2:
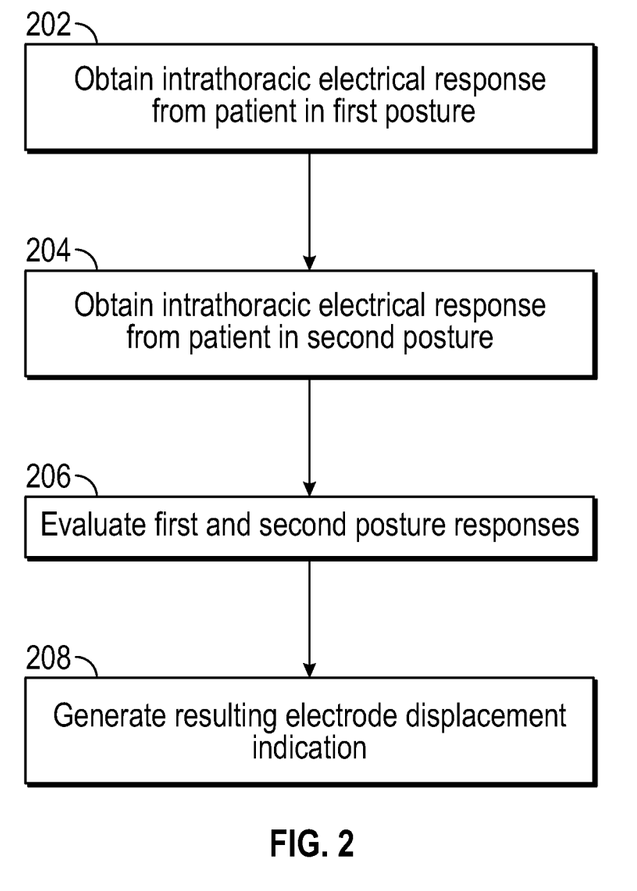
FIG. 2 shows an example of how electrode displacement can be determined.

FIG. 2 shows an example of how electrode displacement can be determined. At 202, an intrathoracic electrical response signal (e.g., thoracic impedance or other physiological conductivity characteristic) can be obtained from a subject in a first posture during a first time period, such as in response to a delivered electrical test stimulus, such as a subcapture test stimulus that does not elicit a heart contraction.

At 204, an intrathoracic electrical response signal (e.g., impedance or other physiological conductivity characteristic) can be obtained from the subject in a second posture (e.g., different from the first posture) during a second time period, such as in response to a delivered electrical test stimulus, such as a subcapture test stimulus that does not elicit a heart contraction.

The different postures can be determined using a posture sensor 125 or obtaining another suitable direct or indirect indication of the subject's postural position. A detected change in posture (e.g., recumbent to upright, supine to upright, etc.) can be used to trigger the intrathoracic impedance or conductivity response acquisition at 202 and 204, or to trigger analysis of such monitored intrathoracic impedance or conductivity data associated with a posture position shift.

The thoracic impedance or conductivity signal can be signal-processed, such as using a lowpass filter circuit to attenuate or eliminate cardiac contraction ("cardiac stroke") variability and respiratory (breathing) variability components of the thoracic impedance or conductivity signal, while passing or preserving DC or near-DC thoracic fluid status information of the thoracic impedance or conductivity signal. The lowpass filter circuit can be implemented as an analog circuit component, or as a digital filter implementation, such as using the processor or controller circuit 116. The lowpass filter circuit can include a band edge cutoff frequency and one or more lowpass filter pole(s) that can be selected to attenuate or eliminate the cardiac stroke and respiratory variability components of the thoracic impedance or conductivity signal, while preserving the DC or near-DC thoracic fluid status information of the thoracic impedance or conductivity signal. The lowpass filtering can equivalently include averaging, or using a specified feature of a histogram (e.g., a histogram mean), or any other technique that is capable of attenuating or eliminating cardiac contraction or respiratory variability components of the thoracic impedance or conductivity signal, while preserving DC or near-DC thoracic fluid status information of the thoracic impedance or conductivity signal.

The lowpass filter circuit can be implemented as part of a bandpass filter circuit, which can also include one or more highpass filter pole(s) that can be selected, such as to attenuate or eliminate a component of the DC or near-DC thoracic impedance or conductivity fluid status information due to a posture-change related compensatory change in the subject's vascular tone (e.g., vasodilation or vasoconstriction), such as while preserving DC or near-DC thoracic fluid status information that is associated with a posture-change related electrode displacement event.

At 206, the intrathoracic electrical response signal information in the first and second postures can be evaluated, such as by the processor or controller circuit 116. Such evaluation can include comparing a DC or near-DC thoracic impedance or conductivity signal, indicative of thoracic fluid status, in the first posture, to a DC or near-DC thoracic impedance or conductivity signal indicative of thoracic fluid status, in the second posture, such as explained in more detail herein.

At 208, a resulting electrode displacement indication can be generated, such as based on the evaluation at 206, and provided to a user or to an automated process that can generate an alert or otherwise make use of such information.

Figure 3:
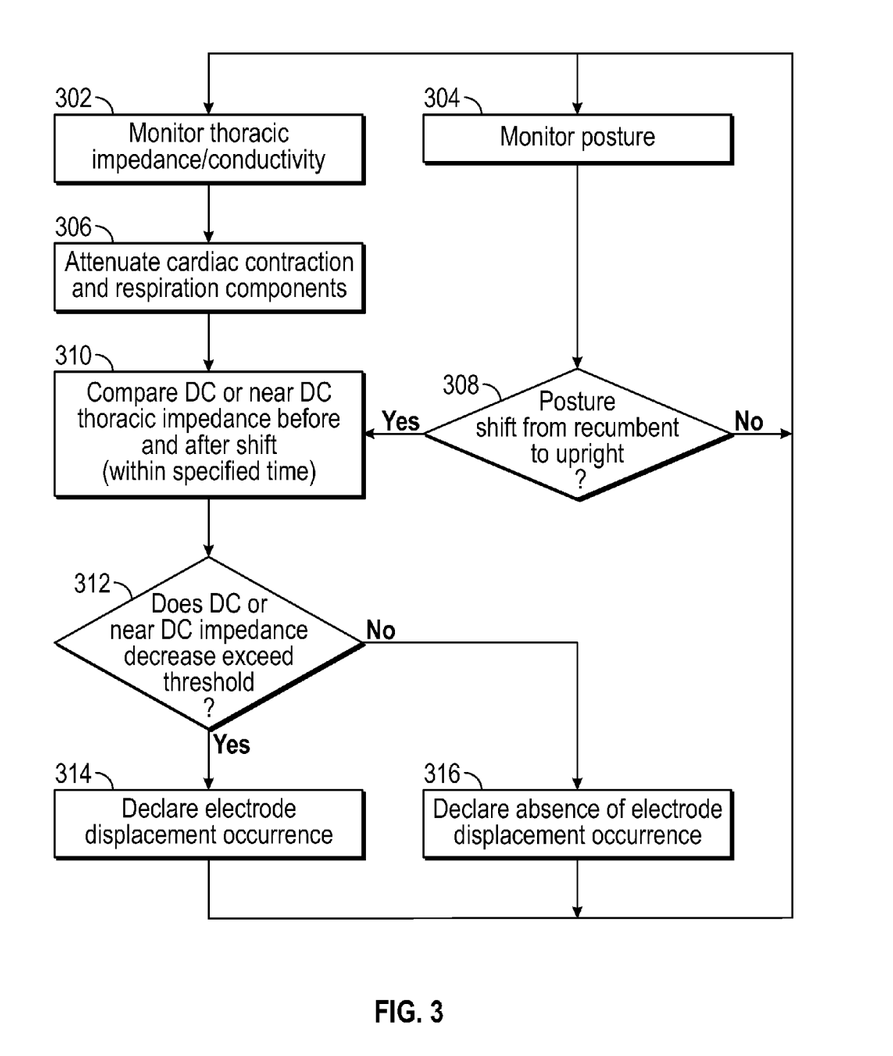
FIG. 3 shows a more particular example of how electrode displacement can be determined.

FIG. 3 shows a more particular example of how electrode displacement can be determined. At 302, thoracic impedance or conductivity can be monitored, such as explained above using a thoracic impedance or conductivity detector, such as can be included in the physiologic sensor 115. Concurrently, at 304, the subject's posture can be monitored, such as explained above, such as by using the posture sensor 125.

At 306, the thoracic impedance or conductivity signal can be lowpass filtered, bandpass filtered, or otherwise signal processed, such as to extract a DC or near DC component of the thoracic impedance or conductivity, indicative of thoracic fluid status, while attenuating or eliminating a cardiac contraction or stroke component of the thoracic impedance or conductivity, and attenuating or eliminating a respiration component of the thoracic impedance or conductivity. This signal processing can optionally include highpass filtering, as explained above, such as to attenuate or eliminate a component of the DC or near-DC thoracic fluid status information due to a posture-change related compensatory change in the subject's vascular tone (e.g., vasodilation or vasoconstriction), while preserving near-DC thoracic fluid status information that is associated with a posture-change related electrode displacement event. The latter is generally more abrupt than the former, and filter characteristics can be selected accordingly, such as to discriminate between the former and the latter.

At 308, if a posture shift (e.g., from recumbent to upright), is detected from the posture monitoring at 304, then, at 310, the DC or near DC component of the thoracic impedance or conductivity indicative of thoracic fluid status can be compared before and after the posture shift. The data used for this comparison can optionally be selected to have been obtained within a specified amount of time of the posture shift. The specified amount of time can be established to be shorter than the amount of time needed for a posture-change related compensatory change in the subject's vascular tone (e.g., vasodilation or vasoconstriction), since such change in vascular tone can impact the thoracic impedance or conductivity fluid status without being related to whether an electrode displacement has occurred as a result of the posture shift. The amount of time needed for a posture-change related compensatory change in the subject's vascular tone can be specified based on data previously acquired from the particular patient, or from a population of patients, or from a subpopulation of patients sharing one or more similar characteristics as the particular patient. The influence of a posture-change related compensatory change in a subject's vascular tone can additionally or alternatively be decreased by highpass filtering, such as explained above.

At 312, in terms of thoracic impedance, if the DC or near DC component of the thoracic impedance indicative of thoracic fluid status decreases by an amount exceeding a specified threshold value, then, at 314, an electrode displacement occurrence can be declared, otherwise, at 316, an absence of an electrode displacement occurrence can be declared. In either case, concurrent posture and thoracic impedance or conductivity monitoring at 302 and 304 can then be resumed.

At 312, explained equivalently in terms of thoracic conductivity, if the DC or near DC component of the thoracic conductivity indicative of thoracic fluid status increases by an amount exceeding a specified threshold value, then, at 314, an electrode displacement occurrence can be declared. Otherwise, at 316, an absence of an electrode displacement occurrence can be declared. In either case, concurrent posture and thoracic impedance or conductivity monitoring at 302 and 304 can then be resumed.

To detect LV/CS electrode displacement, such as can arise from a posture change from recumbent to upright, the thoracic impedance or conductivity can be measured using at least one of the LV/CS electrodes 160A, 160B, 160C, or 160D on the LV/CS lead 138B. The most proximal one of these LV/CS electrodes, 160D, is most likely to exhibit the most significant decrease in impedance due to LV/CS lead pullback in response to a posture change from recumbent to upright. Therefore, the most proximal LV/CS electrode 160D can be used as one of the thoracic impedance or conductivity sensing electrodes for determining whether an LV/CS electrode displacement has occurred. In an illustrative thoracic impedance sensing example, a specified subcapture constant current test stimulus can be delivered between a first LV/CS electrode 160C and housing electrode 135, and a response voltage thereto can be measured between a second LV/CS electrode 160C and the header electrode 137.

The test current can be delivered using a four-phase excitation current waveform, and using a 4-point finite impulse response (FIR) filter demodulator to demodulate the resulting voltage response, or by using a two-phase excitation current waveform, which can also use a 4-point FIR filter demodulator to demodulate the resulting voltage response, such as described and explained in Lyden et al. U.S. Patent Publication No. 2009/0177110, which is incorporated herein by reference in its entirety, including its description of using a 4-point FIR filter demodulator to demodulate a two-phase current excitation stimulus. Ohm's Law can be used to determine a thoracic impedance from the specified test current and the measured response voltage. The cardiac contraction ("stroke") and respiration components of the resulting impedance signal can be attenuated, as explained above, to extract a DC or near-DC impedance or conductivity signal indicative of thoracic fluid status, such as explained herein.

The processor or controller circuit 116 can include a comparator to compare a recumbent-to-upright posture change induced increase in the DC or near-DC fluid status indicating component of thoracic impedance to a specified threshold value. If the increase in the DC or near-DC fluid-status indicating component of thoracic impedance exceeds the specified threshold value, then an occurrence of displacement of the LV/CS electrode used to measure the response voltage (e.g., proximal LV/CS electrode 160D) can be declared, otherwise an absence of an occurrence of such electrode displacement can be declared. The specified threshold value can be determined experimentally from a population of patients, or for the particular patient.

A "differential" response can optionally be used, such as to further enhance specificity of an electrode displacement determination, such as by modifying the approach described above with respect to FIG. 3 to monitor thoracic impedance or conductivity, at 302, using at least two separate channels using corresponding response signal acquisition electrodes that can be located on separate and different intravascular leads. For example, in addition to detecting LV/CS lead dislodgement by measuring impedance using most proximal LV/CS electrode 160D, thoracic impedance can also be measured for an electrode on the RV lead 138A, the distal end of which can often be actively affixed at the RV apex, such as by a screwed-in helical affixation mechanism, or by one or more tines that can become enmeshed with the trabecula at the RV apex. Because an actively-fixated RV lead 138A will generally be less prone to dislodgement and electrode displacement than an LV/CS lead 138B that is being held in place by a spiral shape-memory characteristic, an impedance obtained using a voltage response measured from an electrode (e.g., distal tip electrode 140) on the RV lead 138A can be used as a reference. While the RV impedance or conductivity and the LV/CS impedance or conductivity measurements will generally not be acquired at exactly the same instant in time, the RV and LV/CS impedance or conductivity monitoring can generally be carried out in parallel substantially concurrently, and can be signal-processed similarly, such as to attenuate the cardiac contraction and respiration components. RV and LV/CS near-DC or DC thoracic impedance or conductivity measurements can be evaluated before and after a detected posture shift, such as from recumbent to upright. In a differential response approach, a difference between the RV and LV/CS changes can be compared to the specified threshold, at 312, and if the difference exceeds the specified threshold value, then, at 314, an electrode displacement occurrence can be declared, otherwise an absence of an electrode displacement occurrence can be declared.

More generally, the differential response approach of comparing such a difference (e.g., between RV and LV/CS) in the impedance or conductivity response to a threshold value can be regarded as a particular example of determining a correlation between responses from different leads (e.g., from RV and LV/CS). A large difference in the responses can be regarded as a form of decorrelation between responses.

Further, the above notion and techniques of using a differential response, or indication of correlation between responses from two different leads, can be extended to more than two leads, such as by making pairwise difference or correlation determinations between leads, as explained further herein.

Still further, the above notion and techniques of using a differential response or indication of correlation between responses from two different leads can be extended to using a differential response or indication of correlation between responses from different electrodes on the same intravascular lead. In an example, multiple response signals can be obtained from different sets of one or more electrodes that are longitudinally displaced from each other along a length of an intravascular lead, such as using an LV/CS lead 138B, which can include electrodes 160A, 160B, 160C, and 160D. As an illustrative example, a differential response can be obtained using (1) the most proximal pair of electrodes 160D, 160C for bipolar thoracic impedance or conductivity response sensing, which can be compared against (2) a reference signal constructed using a more distal pair of electrodes 160B, 160A for bipolar thoracic impedance or conductivity response sensing. Other permutations of one or more electrodes on the same intravascular lead can be used, or such other permutations can include one or more electrodes on a different lead, or at housing or a header of the implantable device 102.

Figure 4:
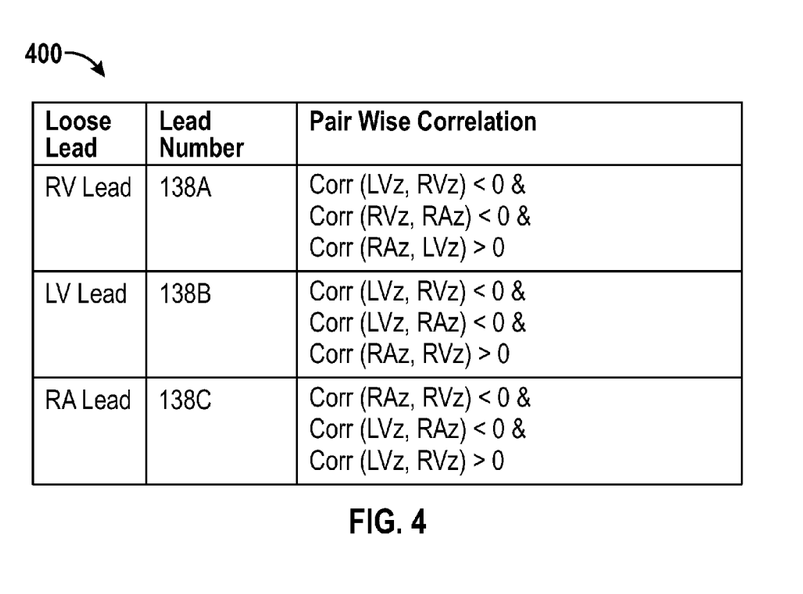
FIG. 4 illustrates an example of using a pair-wise correlation between intrathoracic impedances indicative of fluid status that can be received from the leads.

FIG. 4 illustrates an example 400 of using a pair-wise correlation between intrathoracic impedances indicative of fluid status that can be received from the leads 138A-138C. In FIG. 4, the lead impedance vector for the RV lead 138A can be represented by RVz, the lead impedance vector for the LV/CS lead 138B can be represented by LVz, the lead impedance vector for the RA lead 138C can be represented by RAz. The processor or controller circuit 116 can include or implement an evaluation circuit that can compare pair-wise correlations between 138A, 138B, and 138C leads-based vectors, RVz, LVz, and LAz, over a time period spanning at least one postural transition (e.g., from recumbent to upright), however, a posture sensor 125 is not required for the example shown in FIG. 4, such as explained below.

The processor or controller circuit 116 can declare an occurrence of a displaced RV lead 138A when: (1) the correlation coefficient between the LVz and the RVz lead impedance response is negative; (2) the correlation coefficient between the RVz and the RAz lead impedance response is negative; and (3) the correlation coefficient between the RAz and the LVz lead impedance response is positive.

The processor or controller circuit 116 can declare an occurrence of a displaced LV lead 138B when: (1) the correlation coefficient between the LVz and the RVz lead impedance response is negative; (2) the correlation coefficient between the LVz and the RAz lead impedance response is negative; and (3) the correlation coefficient between the RAz and the RVz lead impedance response is positive.

The processor or controller circuit 116 can declare an occurrence of a displaced RA lead 138C when: (1) the correlation coefficient between the RVz and the RAz impedance response is negative; (2) the correlation coefficient between the LVz and the RAz impedance response is negative; and (3) the correlation coefficient between the LVz and the RVz impedance response is positive.

The technique shown in FIG. 4 can be computed using correlations that can be determined within a specified time before and after a posture shift (e.g., from recumbent to upright), such as described above with respect to FIG. 3. This can provide good specificity, such as where the implantable device 102 includes a posture sensor, such as in the physiologic sensor 115. However, it should be noted that a posture sensor is not required to implement the technique shown in FIG. 4. So long as the lead impedances are monitored over a period of time that is long enough to over a time period spanning at least one postural transition (e.g., from recumbent to upright) the correlations can be computed, and an indication of electrode displacement can be generated from the correlations, even without a specific posture change being specifically detected by a posture sensor, albeit with less specificity than if a posture sensor were available and used to select lead impedance data within a specified time before and after a posture change.

Figure 5:
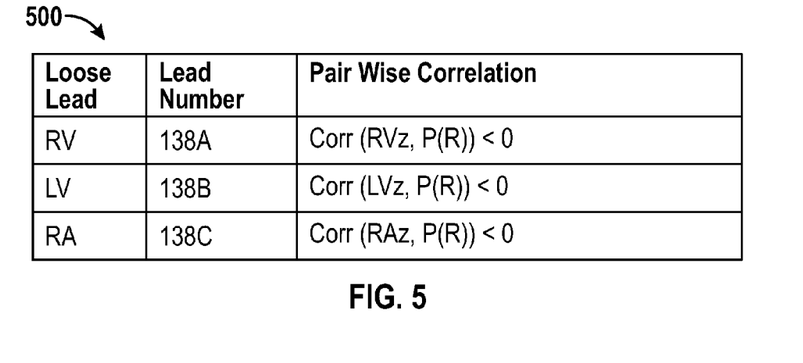
FIG. 5 illustrates an example of using a correlation between intrathoracic impedances received from respective leads and a posture-indicative posture position vector signal.

FIG. 5 illustrates an example 500 of using a correlation between intrathoracic impedances received from respective leads 138A-138C and the posture-indicative posture position vector signal P(R) such as can include information received by the processor or controller circuit 116 from a posture sensor included in the physiologic sensor 115. The posture position vector signal P(R) can represent the expected impedance response for a particular posture change absent an electrode displacement occurrence—for example, a posture change from recumbent to upright would be expected to yield an increase in thoracic impedance as fluid shifts from the thorax toward the lower extremities, in the absence of an electrode displacement (e.g., LV/CS electrode pullback), which, as explained above, can result in an abrupt decrease in thoracic impedance upon transition from a recumbent to upright posture position. In this way, the posture position vector signal can map expected thoracic impedance or conductivity responses to specific state changes.

The processor or controller circuit 116 can declare an occurrence of: (1) a displaced electrode of LV lead 138B when a correlation coefficient between the LVz impedance response and the posture position vector P(R) is negative; (2) a displaced electrode of RA lead 138C when a correlation coefficient between the RAz impedance response and the posture position vector P(R) is negative; and/or (3) a displaced electrode of RV lead 138A when a correlation coefficient between the RAz impedance response and the posture position vector P(R) is negative.

Figure 6:
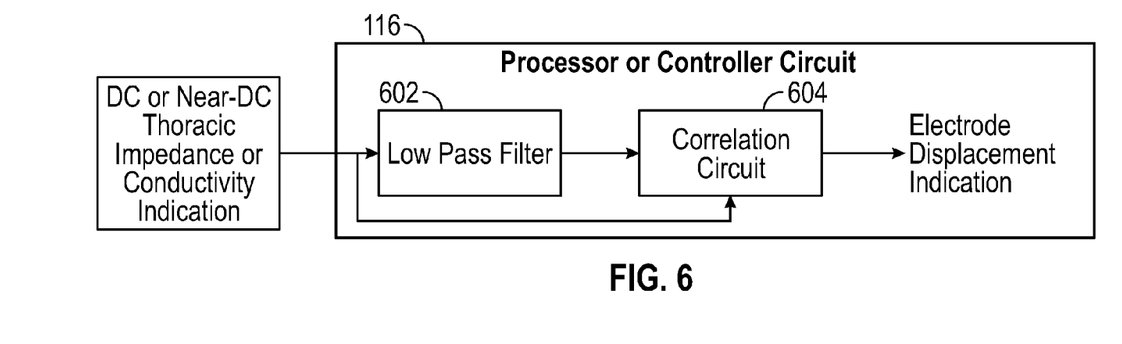
FIG. 6 shows an example of a technique that can be used to compute a functional relationship between posture and an electrical response signal (e.g., DC or near DC thoracic impedance or conductivity) between first and second time periods respectively representing periods before and after a posture shift.

FIG. 6 shows an example of a technique that can be used to compute a functional relationship between posture and an electrical response signal (e.g., DC or near DC thoracic impedance or conductivity) between first and second time periods respectively representing periods before and after a posture shift. The functional relationship can be used to compute an indication of electrode displacement within the subject between the first and second time periods. A posture sensor is not required in this example, but can be used to enhance specificity. In FIG. 6, an input of the processor or controller circuit 116 can receive the DC or near-DC fluid status component of the thoracic impedance or conductivity signal (e.g., after attenuation of the cardiac contraction and respiration components). The processor or controller circuit 116 can include a digital filter, such as a lowpass filter 602. The lowpass filter 602 can include a passband/stopband band edge frequency that can be selected to discriminate between (1) a thoracic impedance response due to a posture shift, and (2) a thoracic impedance response due to an electrode displacement associated with the posture shift.

For example, a posture shift from recumbent to upright will result in a fluid shift away from the thorax toward the lower extremities, which will increase the thoracic impedance, but the time response of such intrabody fluid shift away from the thorax will be appreciably slower than the time response of a thoracic impedance decrease resulting from any LV/CS lead pullback. By selecting a band edge frequency that can pass the former but reject the latter (or vice-versa), discrimination between these two effects can be accomplished, such as by passing the lowpass filtered signal output from the lowpass filter 602 and the unfiltered signal (bypassing lowpass filter 602) into respective first and second inputs of a correlation circuit 604, which can compute a correlation between the respective signals at these two inputs. When a positive correlation exists, then the processor or controller circuit 116 can declare the absence of an electrode displacement occurrence. When a negative correlation exists, then the processor or controller circuit can declare the occurrence of an electrode displacement.

In this example, an explicit posture sensor signal input is not necessary to determine whether an electrode displacement has occurred, so long as the subject does make at least one or more changes in posture. However, if a posture sensor 125 is available in the implantable device 102, the resulting posture information can be used, such as to enhance specificity, for example, by limiting the consideration of DC or near DC thoracic impedance or conductivity data to that obtained within a specified period of time before a shift in posture is detected by the posture sensor 125, within a specified period of time after a shift in posture is detected by the posture sensor 125, or within a specified of time before and after a shift in posture is detected by the posture sensor 125.

Figure 7:
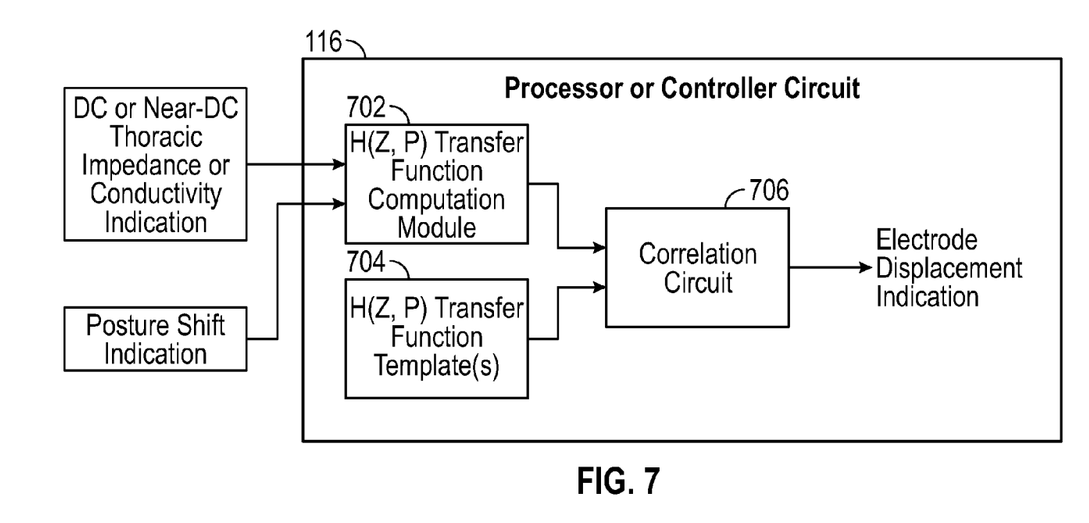
FIG. 7 shows an example of a system response transfer function technique that can be used to compute a functional relationship between posture and an electrical response signal (e.g., DC or near DC thoracic impedance or conductivity) between first and second time periods respectively representing periods before and after a posture shift.

FIG. 7 shows an example of a system response transfer function technique that can be used to compute a functional relationship between posture and an electrical response signal (e.g., DC or near DC thoracic impedance or conductivity) between first and second time periods respectively representing periods before and after a posture shift. The functional relationship can be used to compute an indication of electrode displacement within the subject between the first and second time periods.

In FIG. 7, an input of the processor or controller circuit 116 can receive: (1) the DC or near-DC fluid status component of a thoracic impedance or conductivity signal (e.g., after attenuation of the cardiac contraction and respiration components), such as from a physiologic sensor 115; and (2) a posture shift indication, such as from the posture sensor 125.

The processor or controller circuit 116 can include a H(Z, P) transfer function computation module 702, which can be configured to compute a system response transfer function, such as between a specified change in posture (P) and a resulting DC or near-DC fluid status component of a thoracic impedance or conductivity signal (Z). In an example, H(Z, P) transfer function computation module 702 can be configured to compute a frequency domain transfer function, such as by applying a Fast Fourier Transform (FFT) to a time domain H(Z, P) transfer function.

The processor or controller circuit 116 can include or be coupled to a memory circuit that can include a library of one or more specified H(Z, P) system response transfer function templates to which the H(Z, P) system response transfer function can be compared, such as in the time domain, in the frequency domain, or in both. The comparison can be carried out using a correlation circuit 706. The resulting correlation information can be used to determine whether an electrode displacement has occurred, such as resulting from a posture shift of the patient, as explained above.

The H(Z, P) system response function can be impacted by whether an electrode displacement has occurred, such as resulting from a posture shift of the patient. For example, for a recumbent-to-upright posture shift, in the absence of an electrode displacement, the DC or near-DC fluid status indicating component of the thoracic impedance will generally increase as fluid shifts away from the thorax toward the lower extremities. However, the increase may be limited, offset, or otherwise affected by a compensatory change in the subject's vascular tone (e.g., vasodilation or vasoconstriction). By contrast, if an electrode displacement occurs, such as for LV/CS electrode pullback upon a posture shift from recumbent to upright, the DC or near-DC fluid status indicating component of the thoracic impedance can abruptly decrease—more abruptly than any DC or near-DC impedance change due to intrabody fluid shift or due to vasodilation or vasoconstriction.

The H(Z, P) system response can be analyzed by the processor or controller circuit 116, e.g., in the time domain or in the frequency domain. The difference in time response or frequency response of the H(Z, P) system response transfer function between a posture-shift induced electrode displacement (which will include an abrupt, decreased impedance system response) and a intrabody fluid shift (which will include a slower, increased impedance system response can be used to discriminate between these two conditions, such as by using the correlation circuit 706 to correlate the response to at least one template representative of at least one of these two conditions.

A positive correlation to a narrow bandwidth H(Z,P) system response template indicative of an electrode displacement can be used to declare an occurrence of an electrode displacement. A negative correlation to the narrow bandwidth H(Z, P) system response template indicative of an electrode displacement can be used to declare an absence of an electrode displacement occurrence.

A positive correlation to a broader bandwidth H(Z,P) system response template indicative of an intrabody fluid shift can be used to declare an absence of an occurrence of an electrode displacement. A negative correlation to the broader bandwidth H(Z, P) system response template indicative of an intrabody fluid shift can be used to declare an electrode displacement occurrence.

Correlations to each of the narrow bandwidth and broader bandwidth H(Z, P) system response templates can be used to further enhance the specificity of the electrode displacement determination. For example, an electrode displacement occurrence can be declared when there is a positive correlation to a narrow bandwidth H(Z, P) system response template and a negative correlation to a broader bandwidth H(Z, P) system response template, and an absence of an electrode displacement occurrence can be declared when there is a positive correlation to a broader bandwidth H(Z, P) system response template and a negative correlation to a narrower bandwidth H(Z, P) system response template.

Various Notes & Examples

Example 1 can include can include or use subject matter (such as an apparatus, a method, a means for performing acts, or a device readable medium including instructions that, when performed by the device, can cause the device to perform acts), such as can include or use an apparatus comprising: a processor circuit, which can include: an input, configured to receive an intrathoracic electrical response signal obtained from a subject in response to a delivered subcapture electrical test stimulus, the test stimulus delivered and the response signal obtained during both first and second time periods, in which the subject is in different first and second posture positions during the respective first and second time periods; and an evaluation circuit, operatively coupled to the input, the evaluation circuit configured to process information about a change in the response signal between the first and second time periods to compute an indication of electrode displacement within the subject between the first and second time periods; and an output, configured to provide the indication of electrode displacement to a user or an automated process.

Example 2 can include or use, or can optionally be combined with the subject matter of Example 1, to optionally include or use the input of the processor circuit being configured to receive a posture-indicative signal obtained from a subject during the first and second time periods; wherein the processor can be configured to declare an electrode displacement occurrence, between the first and second time periods, in response to a decrease in thoracic impedance exceeding a specified threshold value, within a specified period of time, when the patient shifts from a recumbent posture position to an upright posture position between the first and second time periods.

Example 3 can include or use, or can optionally be combined with the subject matter of any of Examples 1 or 2, to optionally include or use an implantable medical device, which can be configured to be subcutaneously implantable within the subject, and wherein the implantable medical device can include: the processor circuit; a posture detector circuit, operatively coupled to the processor circuit, the posture detector circuit configured to provide a posture-indicative signal correlative to a posture position of the subject; a thoracic impedance detection circuit, which can be configured to be operatively coupled to a left ventricular coronary sinus (LV/CS) lead electrode to obtain a thoracic impedance signal using the LV/CS lead electrode; and a thoracic fluid detection filter circuit, which can be operatively coupled to the thoracic impedance measurement circuit and the processor circuit, the thoracic fluid detection filter circuit can be configured to attenuate a cardiac contraction component and a respiration component of the thoracic impedance signal to obtain a DC or near-DC thoracic impedance based indication of thoracic fluid status of the subject; and wherein the input of the processor circuit can be configured to receive the posture-indicative signal, and wherein the processor circuit can be configured to declare an electrode displacement occurrence, between the first and second time periods, in response to a decrease in the DC or near-DC thoracic impedance based indication of thoracic fluid status of the subject exceeding a specified threshold value, within a specified period of time, when the posture-indicative signal received from the posture detector circuit indicates that the patient shifts from a recumbent posture position to an upright posture position between the first and second time periods.

Example 4 can include or use, or can optionally be combined with the subject matter of any of Examples 1 through 3, to optionally include or use the intrathoracic electrical response signal including: an intrathoracic electrical first response signal that can be obtained using an electrode located on a first intravascular lead; and an intrathoracic electrical second response signal that can be obtained using an electrode located on a separate second intravascular lead; wherein the evaluation circuit can be configured to detect a change in the first response signal between the first and second time periods, and to detect a change in the second response signal between the first and second time periods, and to evaluate a comparison between the change in the first response signal and the change in the second response signal to compute the indication of electrode displacement within the subject between the first and second time periods.

Example 5 can include or use, or can optionally be combined with the subject matter of any of Examples 1 through 4, to optionally include or use the intrathoracic electrical response signal including an intrathoracic electrical third response signal that can be obtained using an electrode that can be located on a third intravascular lead, separate from the first and second intravascular leads; wherein the evaluation circuit can be configured to detect a change in the third response signal between the first and second time periods, and evaluating a pairwise comparison between the change in the first response signal, the change in the second response signal, and the change in the third response signal to compute the indication of electrode displacement within the subject between the first and second time periods, wherein the indication of electrode displacement is lead-specific.

Example 6 can include or use, or can optionally be combined with the subject matter of any of Examples 1 through 5, to optionally include or use the input of the processor circuit being configured to receive a posture-indicative signal obtained from a subject during the first and second time periods; and the evaluation circuit being configured to declare an electrode displacement occurrence, between the first and second time periods, in response to the posture-indicative signal and the response signal between the first and second time periods.

Example 7 can include or use, or can optionally be combined with the subject matter of any of Examples 1 through 6, to optionally include or use the input of the processor circuit being configured to receive a posture-indicative signal obtained from a subject during the first and second time periods; and the processor being configured declare an electrode displacement occurrence, between the first and second time periods, in response to a correlation between the posture-indicative signal and the response signal between the first and second time periods.

Example 8 can include or use, or can optionally be combined with the subject matter of any of Examples 1 through 7, to optionally include or use the evaluation circuit being configured to compute a functional relationship between posture and the electrical response signal between the first and second time periods, and to evaluate the functional relationship to compute an indication of electrode displacement within the subject between the first and second time periods.

Example 9 can include or use, or can optionally be combined with the subject matter of any of Examples 1 through 8, to optionally include or use the posture detector circuit being operatively coupled to the processor circuit, the posture detector circuit being configured to provide a posture-indicative signal correlative to a posture position of the subject; a thoracic conductivity detection circuit, which can be configured to be operatively coupled to an electrode and of providing a thoracic conductivity signal; and a thoracic fluid detection filter circuit, which can operatively be coupled to the thoracic conductivity detection circuit, the thoracic fluid detection filter circuit can be configured to attenuate a cardiac contraction component and a respiration component of the thoracic impedance signal to obtain a DC or near-DC thoracic conductivity signal indicative of a thoracic fluid status of the subject; and wherein the processor circuit can be configured to use the posture-indicative signal and the thoracic conductivity signal for evaluating the thoracic conductivity signal in response to a change in posture position of the subject to compute an indication of electrode displacement within the subject.

Example 10 can include or use, or can optionally be combined with the subject matter of any of Examples 1 through 9, to optionally include or use a frequency-selective filter circuit, which can be operatively coupled to the thoracic fluid detection circuit to receive the DC or near-DC thoracic conductivity based thoracic conductivity signal, the filter circuit including a filter edge frequency configured to discriminate between posture-induced electrode displacement and posture-induced thoracic fluid shift.

Example 11 can include or use, or can optionally be combined with the subject matter of any of Examples 1 through 10, to optionally include or use a correlation circuit, including a first correlation circuit input operatively coupled to the thoracic fluid detection circuit to receive the DC or near-DC thoracic conductivity based thoracic conductivity signal, a second correlation circuit input operatively coupled to an output of the frequency-selective filter circuit, and configured to compute a correlation between signals at the first and second correlation circuit inputs to compute an indication of electrode displacement within the subject.

Example 12 can include or use, or can optionally be combined with the subject matter of any of Examples 1 through 11, to optionally include or use the response signal being obtained from bipolar electrodes.

Example 13 can include or use, or can optionally be combined with the subject matter of any of Examples 1 through 12, to optionally include or use the response signal including multiple response signals obtained from different sets of electrodes that are longitudinally displaced from each other along a length of an intravascular lead.

Example 14 can include or use (or can optionally be combined with the subject matter of any of Examples 1 through 14 to optionally include or use) subject matter (such as an apparatus, a method, a means for performing acts, or a device readable medium including instructions that, when performed by the device, can cause the device to perform acts), such as can include or use a tangible non-transitory device readable medium or storage device including instructions that, when performed by the device, cause the device to perform the following acts: receiving an intrathoracic electrical response signal obtained from a subject in response to a delivered subcapture electrical test stimulus, the test stimulus delivered and the response signal obtained during both first and second time periods, in which the subject is in different first and second posture positions during the respective first and second time periods; and processing information about a change in the response signal between the first and second time periods to compute an indication of electrode displacement within the subject between the first and second time periods; and providing the indication of electrode displacement to a user or automated process.

Example 15 can include or use, or can optionally be combined with the subject matter of any of Examples 1 through 14, to optionally include or use instructions that, when performed by the device, cause the device to perform the following acts: receiving a posture-indicative signal obtained from the subject during the first and second time periods; and declaring an electrode displacement occurrence, between the first and second time periods, in response to a decrease in thoracic impedance exceeding a specified threshold value, within a specified period of time, when the patient shifts from a recumbent posture position to an upright posture position between the first and second time periods.

Example 16 can include or use, or can optionally be combined with the subject matter of any of Examples 1 through 15, to optionally include or use instructions that, when performed by the device, cause the device to perform the following acts: receiving thoracic impedance signal obtained using a left ventricular/coronary sinus (LV/CS) lead electrode; and attenuating a cardiac contraction component and a respiration component of the thoracic impedance signal to obtain a DC or near-DC thoracic impedance based indication of thoracic fluid status of the subject; and declaring an electrode displacement occurrence, between the first and second time periods, in response to a decrease in the DC or near-DC thoracic impedance based indication of thoracic fluid status of the subject exceeding a specified threshold value, within a specified period of time, when the posture-indicative signal received from the posture detector circuit indicates that the patient shifts from a recumbent posture position to an upright posture position between the first and second time periods.

Example 17 can include or use, or can optionally be combined with the subject matter of any of Examples 1 through 16, to optionally include or use instructions that, when performed by the device, cause the device to perform the following acts: receiving the intrathoracic electrical response signal, including receiving: an intrathoracic electrical first response signal obtained using an electrode located on a first intravascular lead; and an intrathoracic electrical second response signal obtained using an electrode located on a separate second intravascular lead; detecting a change in the first response signal between the first and second time periods; detecting a change in the second response signal between the first and second time periods; and evaluating a comparison between the change in the first response signal and the change in the second response signal to compute the indication of electrode displacement within the subject between the first and second time periods.

Example 18 can include or use, or can optionally be combined with the subject matter of any of Examples 1 through 17, to optionally include or use instructions that, when performed by the device, cause the device to perform the following acts: receiving the intrathoracic electrical response signal, including receiving an intrathoracic electrical third response signal obtained using an electrode located on a third intravascular lead, separate from the first and second intravascular leads; detecting a change in the third response signal between the first and second time periods; and evaluating a pairwise comparison between the change in the first response signal, the change in the second response signal, and the change in the third response signal to compute the indication of electrode displacement within the subject between the first and second time periods, wherein the indication of electrode displacement is lead-specific.

Example 19 can include or use, or can optionally be combined with the subject matter of any of Examples 1 through 18, to optionally include or use instructions that, when performed by the device, cause the device to perform the following acts: receiving a posture-indicative signal obtained from the subject during the first and second time periods; and declaring an electrode displacement occurrence, between the first and second time periods, in response to the posture-indicative signal and the response signal between the first and second time periods.

Example 20 can include or use, or can optionally be combined with the subject matter of any of Examples 1 through 19, to optionally include or use instructions that, when performed by the device, cause the device to perform the following acts: declaring an electrode displacement occurrence, between the first and second time periods, in response to a computed correlation between the posture-indicative signal and the response signal between the first and second time periods.

Example 21 can include or use, or can optionally be combined with the subject matter of any of Examples 1 through 20, to optionally include or use instructions that, when performed by the device, cause the device to perform the following acts: computing a functional relationship between posture and the electrical response signal between the first and second time periods; and evaluating the functional relationship to compute an indication of electrode displacement within the subject between the first and second time periods.

Example 22 can include or use (or can optionally be combined with the subject matter of any of Examples 1 through 20 to optionally include or use) subject matter (such as an apparatus, a method, a means for performing acts, or a device readable medium including instructions that, when performed by the device, can cause the device to perform acts), such as can include or use receiving, an intrathoracic electrical response signal obtained from a subject, using a left ventricular/coronary sinus (LV/CS) lead electrode, in response to a delivered subcapture electrical test stimulus, the test stimulus delivered and the response signal obtained during both first and second time periods, in which the subject is in different first and second posture positions during the respective first and second time periods; attenuating a cardiac contraction component and a respiration component of the response signal to obtain a DC or near-DC thoracic conductivity based indication of thoracic fluid status of the subject; receiving a posture-indicative signal from the subject during the first and second time periods; declaring an electrode displacement occurrence, between the first and second time periods, in response to an impedance decrease in the DC or near-DC thoracic conductivity based indication of thoracic fluid status of the subject exceeding a specified threshold value, within a specified period of time, when the posture-indicative signal indicates that the patient shifts from a recumbent posture position to an upright posture position between the first and second time periods.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or device-readable medium or device-readable storage device encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible device-readable media or device-readable storage device, such as during execution or at other times. Examples of these tangible device-readable media or device-readable storage devices can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus comprising:
    a processor circuit, including:
        an input, configured to receive an intrathoracic electrical response signal obtained from a subject in response to a delivered subcapture electrical test stimulus, the test stimulus delivered and the response signal obtained during both first and second time periods, in which the subject is in different first and second posture positions during the respective first and second time periods; and
        an evaluation circuit, operatively coupled to the input, the evaluation circuit configured to process information about a change in the response signal between the first and second time periods to compute an indication of electrode displacement within the subject between the first and second time periods using a shift between the different first and second posture positions between the respective first and second time periods; and
        an output, configured to provide the indication of electrode displacement to a user or an automated process.

2. The apparatus of claim 1, wherein:
    the input of the processor circuit is configured to receive a posture-indicative signal obtained from a subject during the first and second time periods; wherein
    the processor is configured to declare an electrode displacement occurrence, between the first and second time periods, in response to a decrease in thoracic impedance exceeding a specified threshold value, within a specified period of time, when the patient shifts from a recumbent posture position to an upright posture position between the first and second time periods.

3. The apparatus of claim 2, wherein the apparatus includes an implantable medical device, configured to be subcutaneously implantable within the subject, and wherein the implantable medical device includes:
    the processor circuit;
    a posture detector circuit, operatively coupled to the processor circuit, the posture detector circuit configured to provide a posture-indicative signal correlative to a posture position of the subject;
    a thoracic impedance detection circuit, configured to be operatively coupled to a left ventricular coronary sinus (LV/CS) lead electrode to obtain a thoracic impedance signal using the LV/CS lead electrode; and
    a thoracic fluid detection filter circuit, operatively coupled to the thoracic impedance measurement circuit and the processor circuit, the thoracic fluid detection filter circuit configured to attenuate a cardiac contraction component and a respiration component of the thoracic impedance signal to obtain a DC or near-DC thoracic impedance based indication of thoracic fluid status of the subject; and
    wherein the input of the processor circuit is configured to receive the posture-indicative signal, and wherein the processor circuit is configured to declare an electrode displacement occurrence, between the first and second time periods, in response to a decrease in the DC or near-DC thoracic impedance based indication of thoracic fluid status of the subject exceeding a specified threshold value, within a specified period of time, when the posture-indicative signal received from the posture detector circuit indicates that the patient shifts from a recumbent posture position to an upright posture position between the first and second time periods.

4. The apparatus of claim 1,
wherein the intrathoracic electrical response signal includes:
an intrathoracic electrical first response signal obtained using an electrode located on a first intravascular lead; and
an intrathoracic electrical second response signal obtained using an electrode located on a separate second intravascular lead;
wherein the evaluation circuit is configured to detect a change in the first response signal between the first and second time periods, and to detect a change in the second response signal between the first and second time periods, and to evaluate a comparison between the change in the first response signal and the change in the second response signal to compute the indication of electrode displacement within the subject between the first and second time periods.

5. The apparatus of claim 4,
wherein the intrathoracic electrical response signal includes an intrathoracic electrical third response signal obtained using an electrode located on a third intravascular lead, separate from the first and second intravascular leads;
wherein the evaluation circuit is configured to detect a change in the third response signal between the first and second time periods, and evaluating a pairwise comparison between the change in the first response signal, the change in the second response signal, and the change in the third response signal to compute the indication of electrode displacement within the subject between the first and second time periods, wherein the indication of electrode displacement is lead-specific.

6. The apparatus of claim 1, wherein:
the input of the processor circuit is configured to receive a posture-indicative signal obtained from a subject during the first and second time periods; and
the evaluation circuit is configured to declare an electrode displacement occurrence, between the first and second time periods, in response to the posture-indicative signal and the response signal between the first and second time periods.

7. The apparatus of claim 6, wherein:
the input of the processor circuit is configured to receive a posture-indicative signal obtained from a subject during the first and second time periods; and
the processor is configured declare an electrode displacement occurrence, between the first and second time periods, in response to a correlation between the posture-indicative signal and the response signal between the first and second time periods.

8. The apparatus of claim 1, wherein the evaluation circuit is configured to compute a functional relationship between posture and the electrical response signal between the first and second time periods, and to evaluate the functional relationship to compute an indication of electrode displacement within the subject between the first and second time periods.

9. The apparatus of claim 1, comprising:
a posture detector circuit, operatively coupled to the processor circuit, the posture detector circuit configured to provide a posture-indicative signal correlative to a posture position of the subject;
a thoracic conductivity detection circuit, configured to be operatively coupled to an electrode and of providing a thoracic conductivity signal; and
a thoracic fluid detection filter circuit, operatively coupled to the thoracic conductivity detection circuit, the thoracic fluid detection filter circuit configured to attenuate a cardiac contraction component and a respiration component of the thoracic impedance signal to obtain a DC or near-DC thoracic conductivity signal indicative of a thoracic fluid status of the subject; and
wherein the processor circuit is configured to use the posture-indicative signal and the thoracic conductivity signal for evaluating the thoracic conductivity signal in response to a change in posture position of the subject to compute an indication of electrode displacement within the subject.

10. The apparatus of claim 9, further comprising:
a frequency-selective filter circuit, operatively coupled to the thoracic fluid detection circuit to receive the DC or near-DC thoracic conductivity based thoracic conductivity signal, the filter circuit including a filter edge frequency configured to discriminate between posture-induced electrode displacement and posture-induced thoracic fluid shift.

11. The apparatus of claim 10, further comprising:
a correlation circuit, including a first correlation circuit input operatively coupled to the thoracic fluid detection circuit to receive the DC or near-DC thoracic conductivity based thoracic conductivity signal, a second correlation circuit input operatively coupled to an output of the frequency-selective filter circuit, and configured to compute a correlation between signals at the first and second correlation circuit inputs to compute an indication of electrode displacement within the subject.

12. The apparatus of claim 1, wherein the response signal is obtained from bipolar electrodes.

13. The apparatus of claim 1, wherein the response signal includes multiple response signals obtained from different sets of electrodes that are longitudinally displaced from each other along a length of an intravascular lead.

14. A tangible non-transitory device readable medium including instructions that, when performed by the device, cause the device to perform the following acts:
receiving an intrathoracic electrical response signal obtained from a subject in response to a delivered sub-capture electrical test stimulus, the test stimulus delivered and the response signal obtained during both first and second time periods, in which the subject is in different first and second posture positions during the respective first and second time periods; and
processing information about a change in the response signal between the first and second time periods to compute an indication of electrode displacement within the subject between the first and second time periods using a shift between the different first and second posture positions between the respective first and second time periods; and
providing the indication of electrode displacement to a user or automated process.

15. The tangible non-transitory device readable medium of claim 14, including instructions that, when performed by the device, cause the device to perform the following acts:
receiving a posture-indicative signal obtained from the subject during the first and second time periods; and
declaring an electrode displacement occurrence, between the first and second time periods, in response to a decrease in thoracic impedance exceeding a specified threshold value, within a specified period of time, when the patient shifts from a recumbent posture position to an upright posture position between the first and second time periods.

16. The tangible non-transitory device readable medium of claim 15, including instructions that, when performed by the device, cause the device to perform the following acts:

receiving thoracic impedance signal obtained using a left ventricular/coronary sinus (LV/CS) lead electrode; and attenuating a cardiac contraction component and a respiration component of the thoracic impedance signal to obtain a DC or near-DC thoracic impedance based indication of thoracic fluid status of the subject; and declaring an electrode displacement occurrence, between the first and second time periods, in response to a decrease in the DC or near-DC thoracic impedance based indication of thoracic fluid status of the subject exceeding a specified threshold value, within a specified period of time, when the posture-indicative signal received from the posture detector circuit indicates that the patient shifts from a recumbent posture position to an upright posture position between the first and second time periods.

17. The tangible non-transitory device readable medium of claim 16, including instructions that, when performed by the device, cause the device to perform the following acts:

receiving the intrathoracic electrical response signal, including receiving:

an intrathoracic electrical first response signal obtained using an electrode located on a first intravascular lead; and an intrathoracic electrical second response signal obtained using an electrode located on a separate second intravascular lead;

detecting a change in the first response signal between the first and second time periods;

detecting a change in the second response signal between the first and second time periods; and evaluating a comparison between the change in the first response signal and the change in the second response signal to compute the indication of electrode displacement within the subject between the first and second time periods.

18. The tangible non-transitory device readable medium of claim 17, including instructions that, when performed by the device, cause the device to perform the following acts:

receiving the intrathoracic electrical response signal, including receiving an intrathoracic electrical third response signal obtained using an electrode located on a third intravascular lead, separate from the first and second intravascular leads;

detecting a change in the third response signal between the first and second time periods; and evaluating a pairwise comparison between the change in the first response signal, the change in the second response signal, and the change in the third response signal to compute the indication of electrode displacement within the subject between the first and second time periods, wherein the indication of electrode displacement is lead-specific.

19. The tangible non-transitory device readable medium of claim 14, including instructions that, when performed by the device, cause the device to perform the following acts:

receiving a posture-indicative signal obtained from the subject during the first and second time periods; and declaring an electrode displacement occurrence, between the first and second time periods, in response to the posture-indicative signal and the response signal between the first and second time periods.

20. The tangible non-transitory device readable medium of claim 19, including instructions that, when performed by the device, cause the device to perform the following acts:

declaring an electrode displacement occurrence, between the first and second time periods, in response to a computed correlation between the posture-indicative signal and the response signal between the first and second time periods.

* * * * *